United States Patent
Emblidge (10) Patent No.: US 6,667,178 B2
(45) Date of Patent: Dec. 23, 2003

(54) OPTIMIZATION OF CAUSTIC USAGE

(75) Inventor: Robert W. Emblidge, Swarthmore, PA (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 376 days.

(21) Appl. No.: 09/850,625

(22) Filed: May 7, 2001

(65) Prior Publication Data

US 2003/0008403 A1 Jan. 9, 2003

(51) Int. Cl.[7] ........................ G01N 33/00; G01N 35/02; G01N 33/26
(52) U.S. Cl. .......................... 436/140; 436/50; 436/51; 436/52; 436/60
(58) Field of Search .............................. 436/50–52, 60, 436/140

(56) References Cited

U.S. PATENT DOCUMENTS

| | | | |
|---|---|---|---|
| 3,277,185 A | | 10/1966 | Eisenlohr et al. |
| 3,673,070 A | * | 6/1972 | Wiley .......................... 204/558 |
| 3,899,294 A | * | 8/1975 | Magiros ...................... 210/743 |
| 4,262,150 A | | 4/1981 | Pujado |
| 4,262,151 A | | 4/1981 | Pujado |
| 4,312,636 A | * | 1/1982 | Singerman ................... 44/447 |
| 4,859,608 A | * | 8/1989 | Frueh .......................... 436/163 |
| 4,973,766 A | | 11/1990 | Penzo et al. |
| 5,487,816 A | * | 1/1996 | Schulz et al. ................. 203/14 |

FOREIGN PATENT DOCUMENTS

| | | |
|---|---|---|
| CZ | 278858 | 7/1994 |
| EP | 95118762 | 6/1996 |
| JP | 02-270830 | 11/1990 |
| SU | 388224 A | * 10/1973 .......... G01N/31/16 |

OTHER PUBLICATIONS

Bízek, et al, Extraction of Phenols: II. Distribution Data for Binary and Multicomponent Mixtures of Phenols, Countercurrent Extraction Performance and Model Validation, The Canadian Journal of Chemical Engineering, vol. 71, Apr. 1993, 256–263.

Gogoleva, et al, Combined processing of Bituminous and Light Brown Coal Tars, Kok i Khimiya, No. 9 pp. 20–23, 1989.

Wurm, et al, Further Developments of the Process of Removing Phenol from Coke Residual Waste Waters with Podbielniak Extractors. Wasser Luft und Betrieb 13 (1969), Nr. 5, pp. 178–180.

Yakoleva, et al, Extraction–Potentiometric Determination of Phenols in Phenolates, Koks Khim. (1992), pp. 25–27.

Catana, et al, Phenol Extraction from Coke–Chemical Sources, Rev. Chim. (Bucharest) (1990), 41(9), pp. 691–695.

* cited by examiner

Primary Examiner—Maureen M. Wallenhorst
Assistant Examiner—Yelena Gakh
(74) Attorney, Agent, or Firm—Robert A. Koons, Jr.; Mitchell D. Hirsch; Buchanan Ingersoll, P.C.

(57) ABSTRACT

A method for determining the quantity of phenol extracted into an aqueous solution of an alkali metal hydroxide uses a measurement of the pH of the solution, from which the equivalents of phenol relative to alkali metal hydroxide in solution is determined. A method for optimizing the use of an aqueous solution of an alkali metal hydroxide in a phenol recovery process uses pH measured to regulate the feed rate of the aqueous solution.

15 Claims, 6 Drawing Sheets

OPTIMIZATION OF CAUSTIC USAGE

FIELD OF THE INVENTION

The present invention relates generally to extractive processes using aqueous solutions of alkali metal hydroxides to recover phenol from organic streams. More particularly, the present invention relates to a method for determining the quantity of phenol that has been extracted into an aqueous solution of an alkali metal hydroxide. The invention also relates to the optimization of an extractive process for the recovery of phenol from various distillation streams by monitoring the pH of an aqueous extraction solvent containing an alkali metal hydroxide.

BACKGROUND OF THE INVENTION

For a number of years, it has been common practice in phenol manufacturing facilities to use aqueous solutions of alkali metal hydroxides to recover phenol from organic streams, such as distillation overheads or bottoms, by extraction into the aqueous stream. This method operates by reaction of the phenol with the alkali metal hydroxide to form a water soluble alkali metal phenate, such as sodium phenate. The basic process by which phenol is converted into sodium phenate is shown by the equation;

$$1\ PhOH + 1\ NaOH \rightarrow 1\ PhO^-Na^+ + 1\ H_2O$$

As the free sodium hydroxide is consumed by conversion to sodium phenate, the pH of the aqueous solution decreases.

Historically, alkali metal hydroxide solutions have been used to extract phenol from an organic stream in an equimolar proportion to the amount of alkali metal hydroxide present in the aqueous stream. That is, as in the example shown, one mole of sodium hydroxide reacts with one mole of phenol to produce one mole of sodium phenate, which is extracted into the aqueous stream.

It is disclosed in U.S. Pat. Nos. 3,277,185 and 4,973,766 that solutions of alkali metal phenate can act as a solvent for free phenol, causing the phenol to have a greater affinity for the aqueous stream. Thus, it is possible to extract greater than an equimolar amount of phenol into an aqueous stream from an organic stream. This phenol is extracted into the aqueous stream as free solubilized phenol, rather than phenate. U.S. Pat. No. 3,277,185 discloses using an aqueous solution of alkali metal phenate at a concentration of 20 to 40% as an extraction solvent to remove phenol from neutral oils in a process for the gasification of solid fuels. U.S. Pat. No. 4,973,766 discloses the use of aqueous solutions of an alkali metal phenate at concentrations of 5 to 15% to extract phenol from a rectification purge containing 20 to 95% phenol.

The goal of a phenol recovery unit is to remove the maximum amount of phenol possible from the organic stream being treated at minimum cost. It is therefore desirable to take advantage of the ability of solutions of alkali metal phenate to absorb free phenol, in a phenol recovery system that uses aqueous solutions of alkali metal hydroxides as an extracting solvent. By doing so the quantity of alkali metal hydroxide used in phenol recovery processes can be significantly reduced. However, since free phenol is not infinitely soluble in aqueous solutions of alkali metal phenate, an underage of alkali metal hydroxide would result in undesirable loss of phenol to the organic effluent. Also, since the organic streams treated in this fashion often have value themselves, it is desirable to produce an organic effluent stream that is essentially free of phenol. Therefore, in order to ensure cost efficiency and maximum removal of phenol from the organic stream, care must be taken to ensure that an appropriate quantity of aqueous alkali metal hydroxide is used in the recovery process.

Accordingly, it is desirable to provide a method for determining the quantity of phenol that has been extracted into an aqueous solution of an alkali metal hydroxide. Further, it is desirable to provide a method for regulating the quantity of aqueous alkali metal hydroxide used in phenol recovery operations to ensure maximum recovery of phenol, acceptable organic effluent and cost effectiveness.

SUMMARY OF THE INVENTION

It is an object of the present invention to provide a method for determining the quantity of phenol that has been extracted into an aqueous solution of an alkali metal hydroxide.

It is another object of the present invention to provide a method for optimizing the use of an aqueous solution of an alkali metal hydroxide in a process for recovering phenol from an organic stream, based on the pH of the aqueous stream at, at least, one point in the system.

It is a further object of the present invention to provide an apparatus for optimizing the use of an aqueous solution of an alkali metal hydroxide in a process for recovering phenol from an organic stream, based on the pH of the aqueous stream at, at least, one point in the system.

In accordance with one embodiment of the invention, a method for indirectly determining the quantity of phenol that has been extracted into an aqueous solution of an alkali metal hydroxide is provided. In this method, aqueous solutions of an alkali metal hydroxide of known concentration, e.g. 20% sodium hydroxide, are titrated with phenol. The pH data collected is used to develop a curve showing solution pH relative to phenol concentration. The curve thus developed is used to determine phenol concentrations in aqueous solutions of alkali metal hydroxides by simply measuring pH.

In accordance with another embodiment of the present invention, a method is provided for regulating the rate at which an aqueous solution of alkali metal hydroxide is fed to a phenol recovery unit as an extracting solvent in countercurrent flow to a phenol containing organic stream. The pH of the aqueous stream is monitored at, at least one point, in the phenol recovery unit. Based on the pH of the aqueous stream, it is possible to determine the concentration of phenol in the aqueous stream and if any free phenol is present in the aqueous stream. The flow of aqueous alkali metal hydroxide to the unit can then be held constant, increased or decreased accordingly to optimize the recovery of phenol and usage of aqueous extracting solvent. The phenol containing organic stream preferably comprises either cumene or α-methyl styrene.

In a further embodiment of the current invention, an apparatus is provided, which makes use of the inventive methods herein disclosed. The apparatus is a unit, which uses an aqueous solution of an alkali metal hydroxide for recovering phenol from an organic stream, such as distillation overheads or bottoms. The feed rate of the alkali metal hydroxide to the unit is regulated by measuring the pH at, at least, one point in the unit and adjusting the feed rate accordingly.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

An embodiment of the present invention provides a method for determining the quantity of phenol that has been absorbed by an aqueous solution of sodium hydroxide. Relatively concentrated solutions of sodium hydroxide, caustic, typically have a pH in the range of 13 to 14. As phenol is absorbed into these solutions, the sodium hydroxide is consumed as sodium phenate is formed, causing a drop in pH. Once all of the sodium hydroxide is consumed, additional phenol is absorbed as solubilized free phenol, with a continued drop in solution pH as more phenol is absorbed. Therefore, the pH of the aqueous solution at any given time corresponds to an amount of phenol that has been absorbed into the solution.

Figure 5:
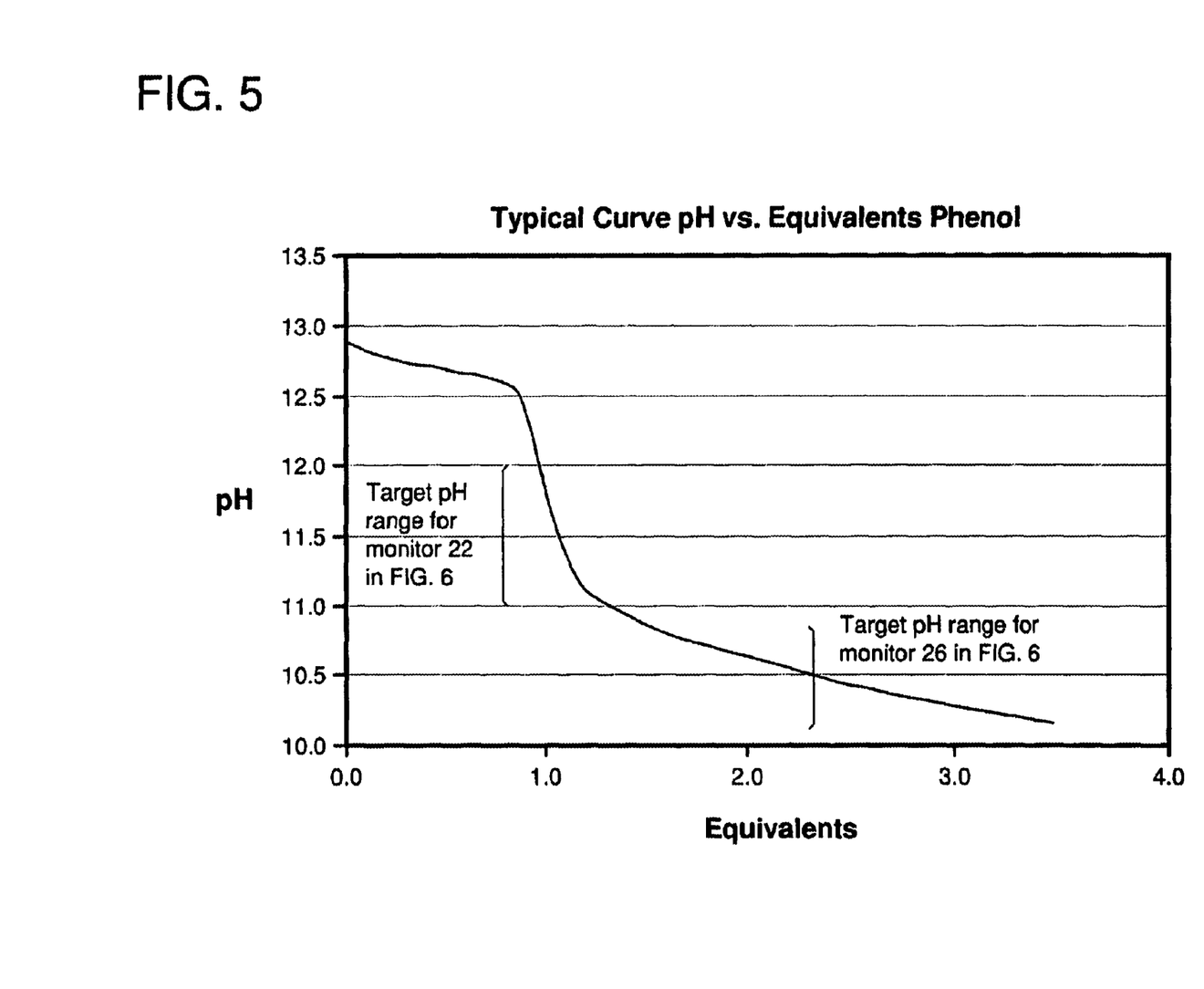
FIG. 5 shows a composite curve relating the pH of an aqueous solution of sodium hydroxide to the equivalents of phenol developed using data from Examples 1–4.

In this embodiment, a curve is developed, which relates the pH of an aqueous solution of sodium hydroxide to the quantity of phenol that has been absorbed into the aqueous solution. The curve, as shown in FIG. 5, is developed by titration of aqueous solutions of sodium hydroxide, at various concentrations, with pure liquid phenol. The curve thus developed can be used to determine the quantity of phenol in an aqueous solution of sodium hydroxide by measuring the pH of the aqueous solution and relating that pH to a point on the curve, which corresponds to a concentration of phenol in the solution.

EXAMPLE 1

Figure 1:
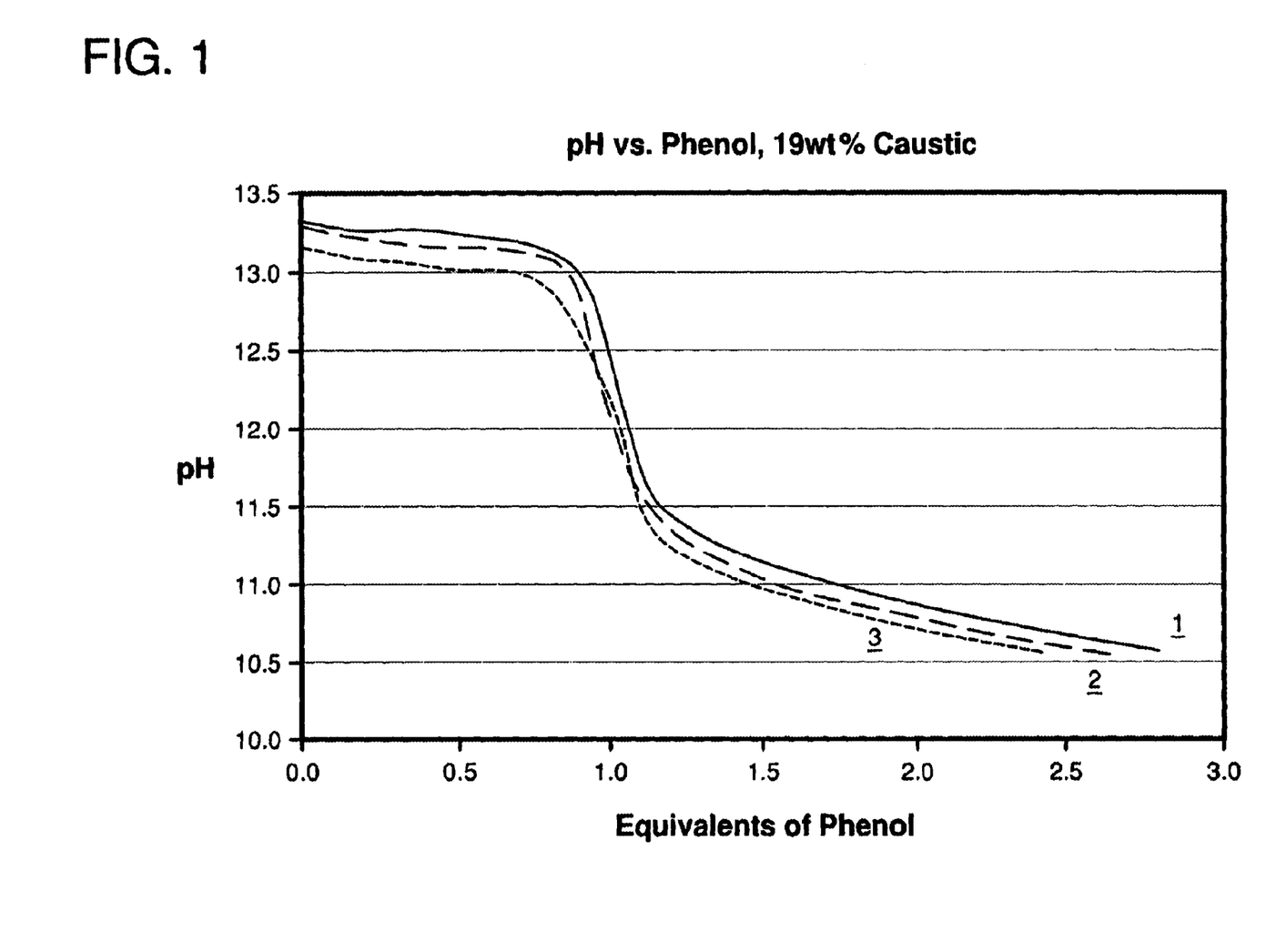
FIG. 1 shows curves relating the pH of an aqueous solution of sodium hydroxide to the equivalents of phenol developed using data from Example 1.

A 19% by weight solution of sodium hydroxide was prepared by dilution of a 46.8% by weight stock solution of sodium hydroxide. A sample of pure phenol was liquefied by heating to the melting point of the solid. The density of the liquid phenol thus prepared was taken as approximately 1.05 gm/mL. A sample of the 19% by weight sodium hydroxide solution was titrated by adding 0.5 mL aliquots to the liquefied phenol to the sodium hydroxide solution with stirring. The pH was measured after each addition and recorded. The data for the trial, which was performed in triplicate, is recorded in TABLE 1. FIG. 1 shows a plot of the pH data from the trials.

EXAMPLE 2

Figure 2:
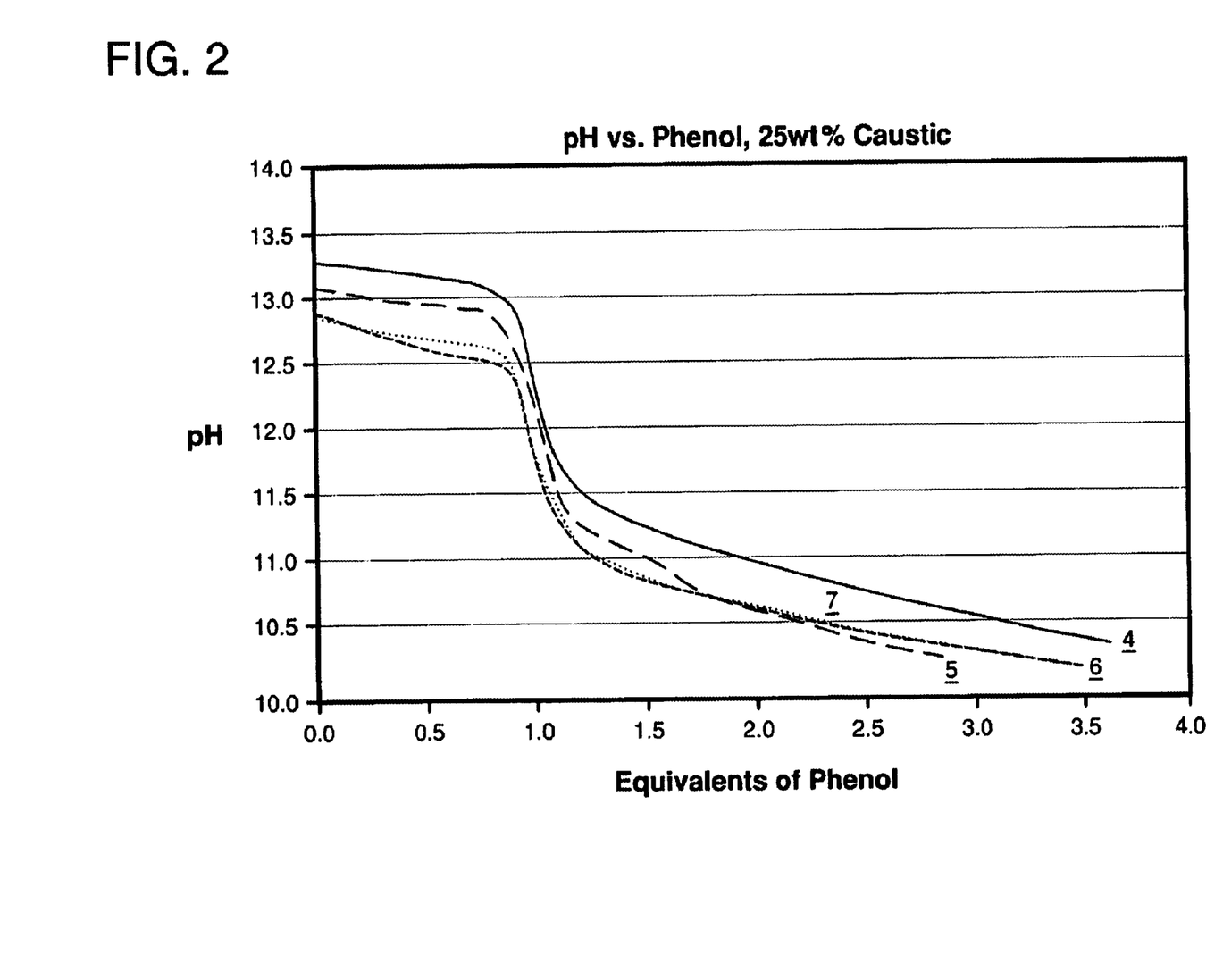
FIG. 2 shows curves relating the pH of an aqueous solution of sodium hydroxide to the equivalents of phenol developed using data from Example 2.

The procedure described in Example 1 was repeated, with the exception that a 25% by weight solution of sodium hydroxide was used. The data for the trial, which was performed in quadruplicate, is recorded in TABLE 2. FIG. 2 shows a plot of the pH data from the trials.

EXAMPLE 3

Figure 3:
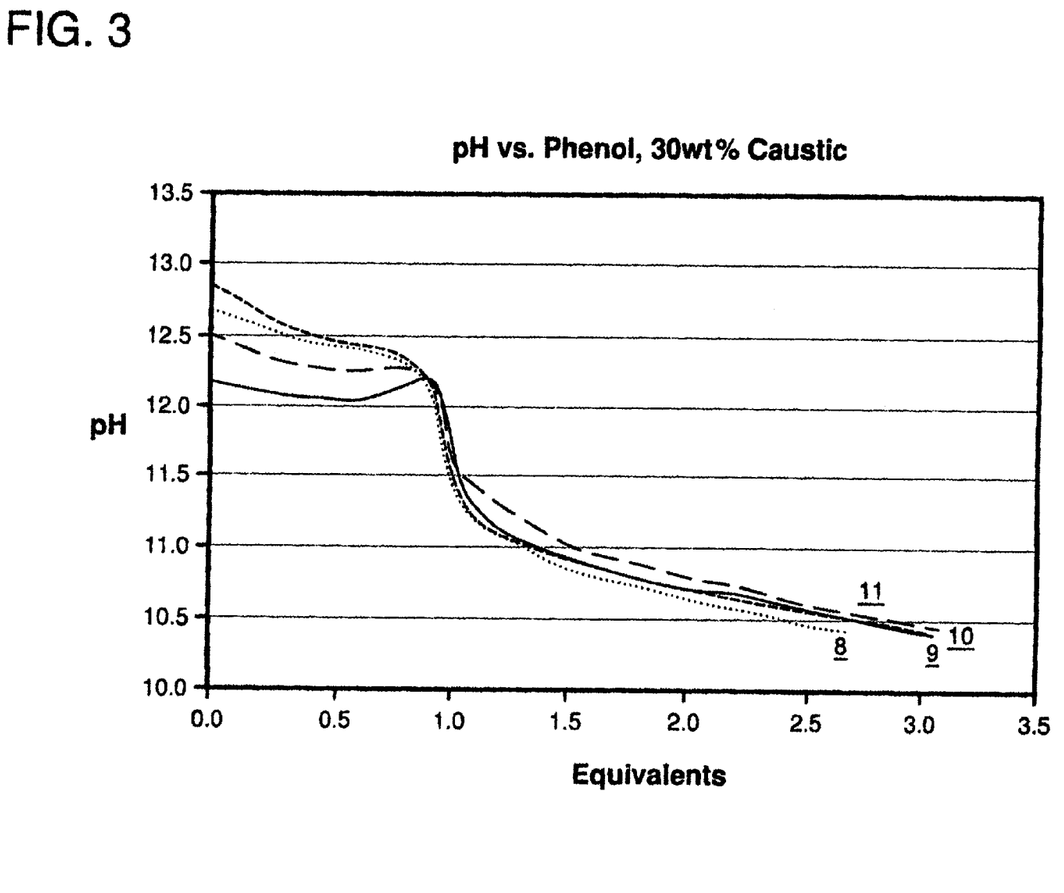
FIG. 3 shows curves relating the pH of an aqueous solution of sodium hydroxide to the equivalents of phenol developed using data from Example 3.

The procedure as described in Example 1 was repeated, with the exception that a 30% by weight solution of sodium hydroxide was used. The data for the trial, which was performed in quadruplicate, is recorded in TABLE 3. FIG. 3 shows a plot of the pH data from the trials.

EXAMPLE 4

Figure 4:
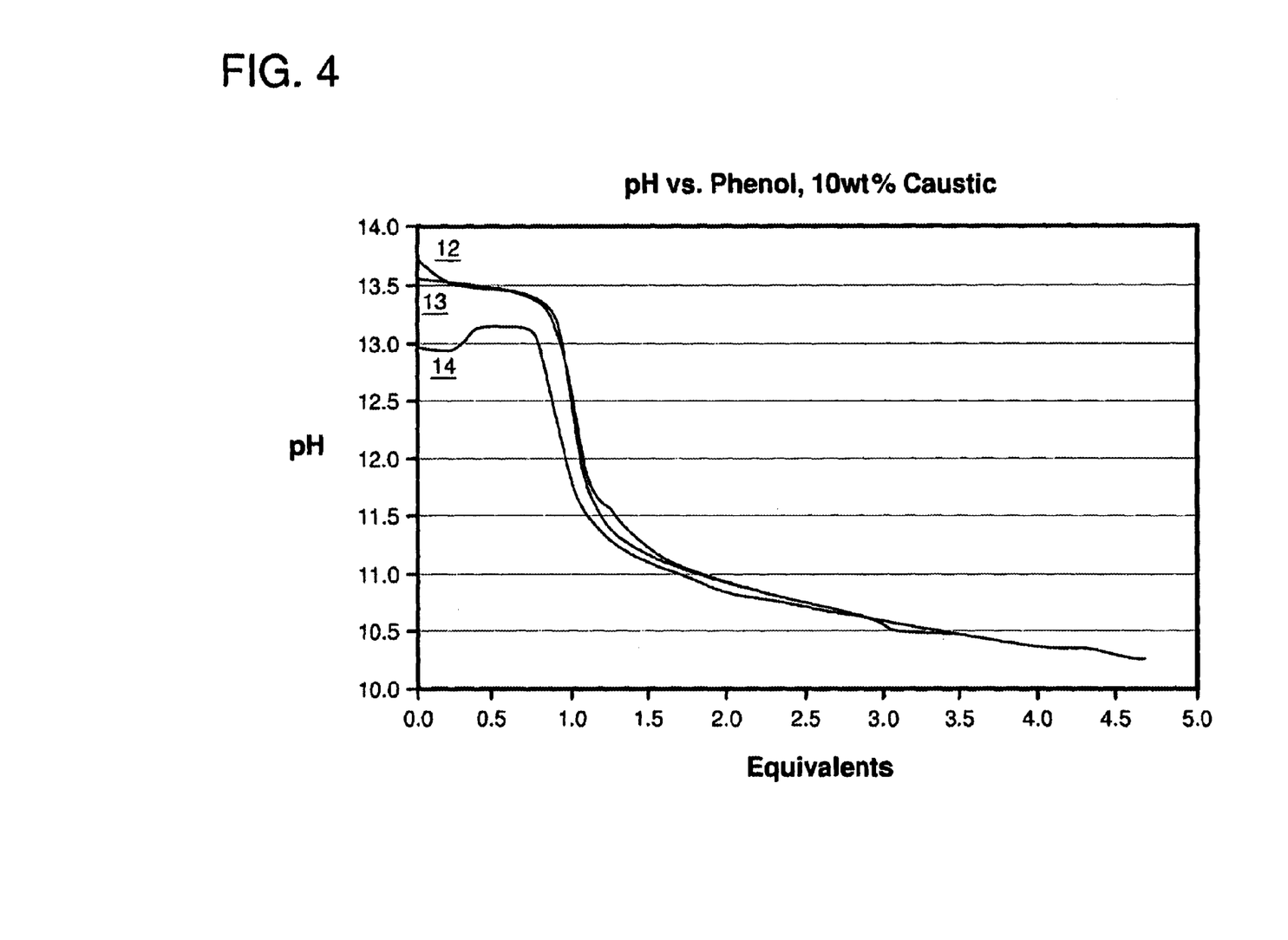
FIG. 4 shows curves relating the pH of an aqueous solution of sodium hydroxide to the equivalents of phenol developed using data from Example 4.

The procedure as described in Example 1 was repeated, with the exception that a 10% by weight solution of sodium hydroxide was used. The data for the trial, which was performed in triplicate, is recorded in TABLE 4. FIG. 4 shows a plot of the pH data from the trials.

TABLE 5 shows the data for all trials at all concentrations at critical concentrations; 1.0, 1.5, 2.0, 2.5 and 3.0 equivalents of phenol relative to sodium hydroxide. It is clear from the data that the pH relative to the equivalents of phenol does not vary as a function of the concentration of aqueous sodium hydroxide used. The largest standard deviation recorded is 0.49, approximately 4%, at the 1.0 equivalent point. Thus, it is possible to use a single curve to relate pH to concentration of phenol, regardless of the concentration of sodium hydroxide used. A composite curve developed from the data compiled in Examples 1 through 4 is shown in FIG. 5.

Using a curve thus developed, it is possible to determine the equivalents of phenol in an aqueous solution relative to sodium hydroxide by simply measuring the pH of the solution and relating the pH to a point on the curve. Once the number of equivalents relative to sodium hydroxide has been determined, the actual quantity of phenol can be calculated using the known concentration of sodium hydroxide.

It will be apparent to those skilled in the art that similar curves can be developed using concentrations of sodium hydroxide other than those reported here. Additionally, it will be apparent that similar curves can be constructed for aqueous bases other than sodium hydroxide, such as potassium hydroxide, lithium hydroxide and calcium hydroxide. Thus, the invention is not limited to the specific embodiment disclosed here.

Figure 6:
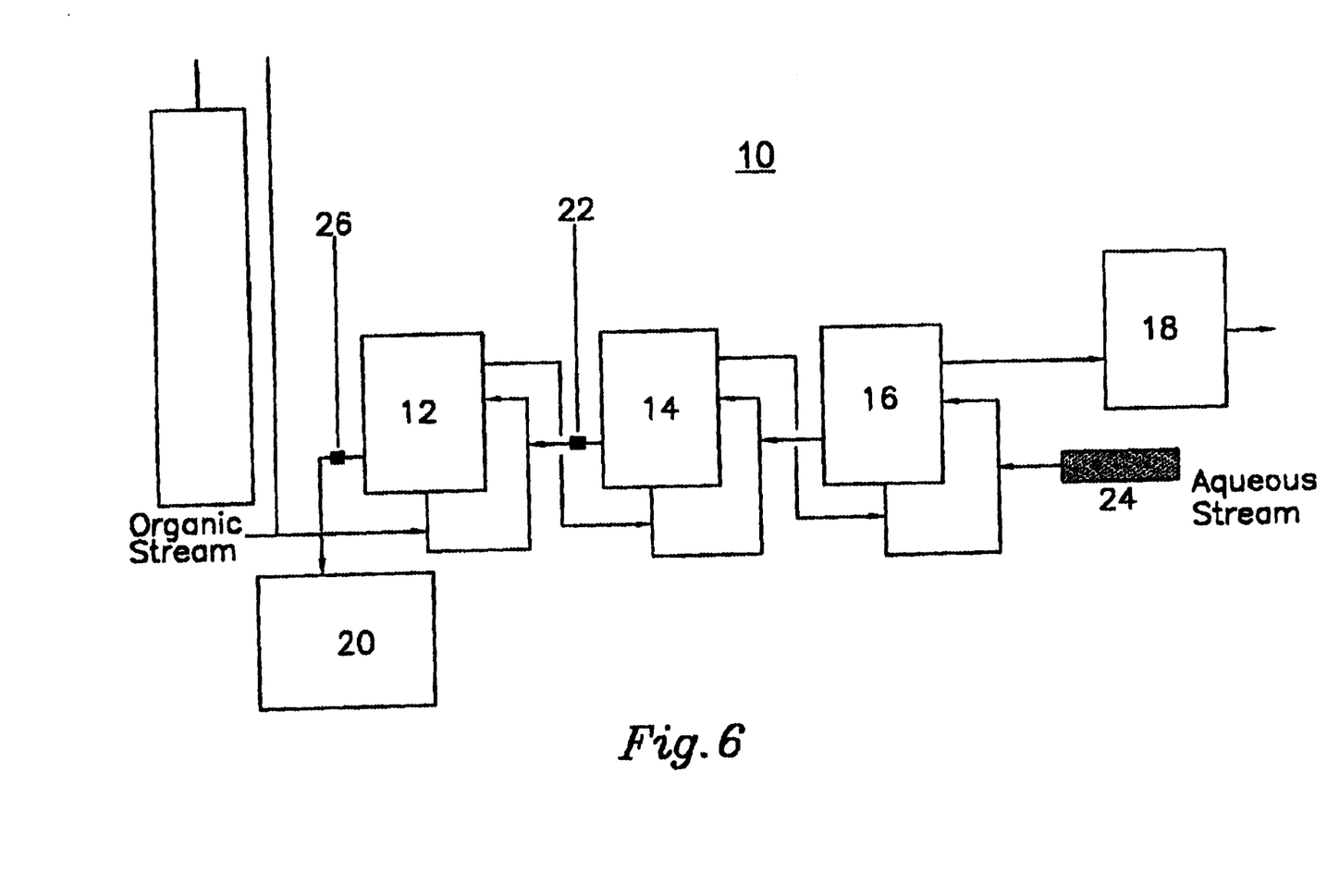
FIG. 6 is a schematic of a phenol recovery unit using the current inventive method.

In another preferred embodiment, the above method is used to regulate the feed rate of an aqueous solution of sodium hydroxide to a multi-stage phenol recovery unit having at least two tanks. An example of this embodiment of the present inventive method is illustrated in FIG. 6. A three stage phenol recovery unit 10 is provided with tanks 12, 14, 16, 18 and 20. A phenol containing organic stream is fed to tank 12 as either distillation overheads or as distillation bottoms from distillation column 30. The organic stream flows continuously from tank 12 to tank 14, then from tank 14 to tank 16, and finally from tank 16 to tank 18. An aqueous solution of sodium hydroxide is fed to tank 16. The aqueous stream flows continuously from tank 16 to tank 14, then from tank 14 to tank 12, and finally from tank 12 to tank 20. As shown in the figure, the organic and aqueous streams contact each other in counter-current fashion in tanks 12, 14 and 16, such that phenol is extracted from the organic stream into the aqueous stream in each tank. A pH monitor 22 for monitoring the pH of the aqueous stream as it exits tank 14 is provided. The monitor may constitute a sampling port for sampling the aqueous stream for laboratory analysis, or it may constitute an in-line pH measurement device. A regulator 24 is provided for regulating the flow of aqueous sodium hydroxide to tank 16.

An acceptable pH range is set for the aqueous stream exiting tank 14 such that the pH range corresponds to a desired concentration of phenol relative to the initial concentration of free sodium hydroxide in the aqueous stream fed to the unit. A pH that is above the acceptable range corresponds to an overage of sodium hydroxide. A pH below the acceptable range corresponds to an underage of sodium hydroxide.

The regulator 24 is adjusted in response to the pH measured at the monitor 22 such that a detected overage of sodium hydroxide will cause a decrease in the feed rate of sodium hydroxide to tank 16. Conversely, a detected underage of sodium hydroxide will cause an increase the feed rate of sodium hydroxide to tank 16.

In a more preferred embodiment, a three stage phenol recovery unit 10 as shown in FIG. 6 and described above is provided. The acceptable pH range for the aqueous stream exiting tank 14 is set such that it corresponds to approximately 1 equivalent of phenol relative to sodium hydroxide in the aqueous stream. In this case, all or nearly all of the sodium hydroxide in the aqueous phase exiting tank 14 has been consumed. In this embodiment, all phenol extracted from the organic stream in tank 12 is extracted as solubilized free phenol.

In an even more preferred embodiment, a three stage phenol recovery unit 10 as shown in FIG. 6 and described above is provided. An additional pH monitor 26 is provided for monitoring the pH of the aqueous stream as it exits tank 12. The acceptable pH range for the aqueous stream exiting tank 14 is set such that it corresponds to approximately 1 equivalent of phenol relative to sodium hydroxide in the aqueous stream. A second acceptable pH range is set for the aqueous stream as it exits tank 12, which corresponds to a phenol content in the aqueous stream of greater than 1 equivalent. In this embodiment, the pH measurements at both monitors are used jointly to adjust the feed rate of the sodium hydroxide such that a detected overage of sodium hydroxide will cause a decrease in the feed rate of sodium hydroxide to tank 16. Conversely, a detected underage of sodium hydroxide will cause an increase in the feed rate of sodium hydroxide to tank 16.

In a most preferred embodiment of the invention as described above, the concentration of aqueous sodium hydroxide fed to tank 16 is 20% and the organic stream composed primarily of either alpha-methylstyrene or cumene containing from 0.1 to 25% and preferably 0.1 to 12% phenol. The acceptable pH range for the aqueous stream exiting tank 14 is set 11.0 to 12.0 and the acceptable pH range for the aqueous stream exiting tank 12 is 9.7 to 10.7. In this embodiment, all phenol extracted from the organic stream in tank 12 is extracted as solubilized free phenol.

It will be recognized by those skilled in the art that the operation of the inventive method herein disclosed does not depend on the use of aqueous sodium hydroxide as an extracting solvent. Other bases capable of forming water soluble phenates may also be used in conjunction with the current inventive method. It will further be recognized that the current invention is not limited to the specific pH ranges recited. Acceptable pH ranges for operation of the method are determined based on the quantities of phenol to be extracted, the aqueous base used, the locations of the pH monitoring means and the number of stages in the phenol recovery unit.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

TABLE 1

| 19% Sodium Hydroxide | | | | | | | | |
|---|---|---|---|---|---|---|---|---|
| Titration #1 6.32 g caustic | | | Titration #2 6.66 g caustic | | | Titration #3 7.33 g caustic | | |
| pH | mL phenol | equiv. phenol | pH | mL phenol | equiv. phenol | pH | mL phenol | equiv. phenol |
| 13.33 | 0.00 | 0.000 | 13.29 | 0.00 | 0.00 | 13.16 | 0.00 | 0.000 |
| 13.26 | 0.50 | 0.186 | 13.22 | 0.50 | 0.176 | 13.10 | 0.50 | 0.160 |
| 13.27 | 1.00 | 0.372 | 13.17 | 1.00 | 0.353 | 13.06 | 1.00 | 0.320 |
| 13.22 | 1.50 | 0.557 | 13.14 | 1.50 | 0.529 | 13.02 | 1.50 | 0.481 |
| 13.16 | 2.00 | 0.743 | 13.11 | 2.00 | 0.705 | 13.00 | 2.00 | 0.641 |
| 12.92 | 2.50 | 0.929 | 12.94 | 2.50 | 0.882 | 12.89 | 2.50 | 0.801 |
| 11.65 | 3.00 | 1.115 | 11.71 | 3.00 | 1.058 | 12.40 | 3.00 | 0.961 |
| 11.30 | 3.50 | 1.301 | 11.29 | 3.50 | 1.234 | 11.40 | 3.50 | 1.122 |
| 11.14 | 4.00 | 1.487 | 11.10 | 4.00 | 1.411 | 11.14 | 4.00 | 1.282 |
| 11.02 | 4.50 | 1.672 | 10.97 | 4.50 | 1.587 | 11.00 | 4.50 | 1.442 |
| 10.92 | 5.00 | 1.858 | 10.87 | 5.00 | 1.763 | 10.90 | 5.00 | 1.602 |
| 10.83 | 5.50 | 2.044 | 10.79 | 5.50 | 1.940 | 10.81 | 5.50 | 1.762 |
| 10.75 | 6.00 | 2.230 | 10.71 | 6.00 | 2.116 | 10.73 | 6.00 | 1.923 |
| 10.68 | 6.50 | 2.416 | 10.64 | 6.50 | 2.292 | 10.66 | 6.50 | 2.083 |
| 10.62 | 7.00 | 2.602 | 10.58 | 7.00 | 2.469 | 10.61 | 7.00 | 2.243 |
| 10.55 | 7.50 | 2.787 | 10.52 | 7.50 | 2.645 | 10.55 | 7.50 | 2.403 |

TABLE 2

25% Sodium Hydroxide

| Titration #4 5.93 g caustic | | | Titration #5 5.66 g caustic | | | Titration #6 6.16 g caustic | | | Titration #7 8.02 g caustic | | |
|---|---|---|---|---|---|---|---|---|---|---|---|
| pH | mL phenol | equiv. phenol | pH | mL phenol | equiv. phenol | pH | mL phenol | equiv. phenol | pH | mL phenol | equiv. phenol |
| 13.27 | 0.00 | 0.000 | 13.07 | 0.00 | 0.000 | 12.88 | 0.00 | 0.000 | 12.88 | 0.00 | 0.000 |
| 13.25 | 0.50 | 0.151 | 13.03 | 0.50 | 0.158 | 12.80 | 0.50 | 0.145 | 12.80 | 0.50 | 0.111 |
| 13.21 | 1.00 | 0.301 | 12.99 | 1.00 | 0.315 | 12.74 | 1.00 | 0.290 | 12.75 | 1.00 | 0.223 |
| 13.18 | 1.50 | 0.452 | 12.97 | 1.50 | 0.473 | 12.71 | 1.50 | 0.435 | 12.68 | 1.50 | 0.334 |
| 13.15 | 2.00 | 0.602 | 12.92 | 2.00 | 0.631 | 12.67 | 2.00 | 0.580 | 12.64 | 2.00 | 0.445 |
| 13.09 | 2.50 | 0.753 | 12.86 | 2.50 | 0.788 | 12.63 | 2.50 | 0.724 | 12.58 | 2.50 | 0.556 |
| 12.87 | 3.00 | 0.903 | 12.37 | 3.00 | 0.946 | 12.49 | 3.00 | 0.869 | 12.54 | 3.00 | 0.668 |
| 11.88 | 3.50 | 1.054 | 11.46 | 3.50 | 1.104 | 11.70 | 3.50 | 1.014 | 12.50 | 3.50 | 0.779 |
| 11.51 | 4.00 | 1.204 | 11.21 | 4.00 | 1.262 | 11.19 | 4.00 | 1.159 | 12.37 | 4.00 | 0.890 |
| 11.35 | 4.50 | 1.355 | 11.08 | 4.50 | 1.419 | 11.02 | 4.50 | 1.304 | 11.69 | 4.50 | 1.002 |
| 11.24 | 5.00 | 1.505 | 10.95 | 5.00 | 1.577 | 10.91 | 5.00 | 1.449 | 11.25 | 5.00 | 1.113 |
| 11.15 | 5.50 | 1.656 | 10.77 | 5.50 | 1.735 | 10.81 | 5.50 | 1.594 | 11.07 | 5.50 | 1.224 |
| 11.07 | 6.00 | 1.806 | 10.68 | 6.00 | 1.892 | 10.75 | 6.00 | 1.739 | 10.96 | 6.00 | 1.336 |
| 11.00 | 6.50 | 1.957 | 10.61 | 6.50 | 2.050 | 10.70 | 6.50 | 1.884 | 10.88 | 6.50 | 1.447 |
| 10.93 | 7.00 | 2.107 | 10.53 | 7.00 | 2.208 | 10.65 | 7.00 | 2.029 | 10.82 | 7.00 | 1.558 |
| 10.87 | 7.50 | 2.258 | 10.45 | 7.50 | 2.365 | 10.59 | 7.50 | 2.173 | 10.77 | 7.50 | 1.669 |
| 10.81 | 8.00 | 2.408 | 10.38 | 8.00 | 2.523 | 10.53 | 8.00 | 2.318 | 10.71 | 8.00 | 1.781 |
| 10.75 | 8.50 | 2.559 | 10.33 | 8.50 | 2.681 | 10.48 | 8.50 | 2.463 | 10.67 | 8.50 | 1.892 |
| 10.69 | 9.00 | 2.709 | 10.28 | 9.00 | 2.839 | 10.44 | 9.00 | 2.608 | 10.62 | 9.00 | 2.003 |
| 10.64 | 9.50 | 2.860 | | | | 10.39 | 9.50 | 2.753 | 10.59 | 9.50 | 2.115 |
| 10.59 | 10.00 | 3.010 | | | | 10.36 | 10.00 | 2.898 | 10.54 | 10.00 | 2.226 |
| 10.53 | 10.50 | 3.161 | | | | 10.32 | 10.50 | 3.043 | 10.50 | 10.50 | 2.337 |
| 10.48 | 11.00 | 3.311 | | | | 10.29 | 11.00 | 3.188 | 10.47 | 11.00 | 2.448 |
| 10.44 | 11.50 | 3.462 | | | | 10.25 | 11.50 | 3.333 | 10.43 | 11.50 | 2.560 |
| 10.39 | 12.00 | 3.612 | | | | 10.22 | 12.00 | 3.478 | 10.40 | 12.00 | 2.671 |

TABLE 3

30% Sodium Hydroxide

| Titration #8 6.67 g caustic | | | Titration #9 6.33 g caustic | | | Titration #10 6.52 g caustic | | | Titration #11 7.42 g caustic | | |
|---|---|---|---|---|---|---|---|---|---|---|---|
| pH | mL phenol | equiv. phenol | pH | mL phenol | equiv. phenol | pH | mL phenol | equiv. phenol | pH | mL phenol | equiv. phenol |
| 12.68 | 0.00 | 0.000 | 12.18 | 0.00 | 0.000 | 12.51 | 0.00 | 0.000 | 12.86 | 0.00 | 0.000 |
| 12.62 | 0.50 | 0.112 | 12.14 | 0.50 | 0.118 | 12.42 | 0.50 | 0.114 | 12.77 | 0.50 | 0.100 |
| 12.55 | 1.00 | 0.223 | 12.10 | 1.00 | 0.235 | 12.35 | 1.00 | 0.228 | 12.66 | 1.00 | 0.200 |
| 12.48 | 1.50 | 0.335 | 12.06 | 1.50 | 0.353 | 12.29 | 1.50 | 0.342 | 12.58 | 1.50 | 0.301 |
| 12.44 | 2.00 | 0.446 | 12.05 | 2.00 | 0.470 | 12.27 | 2.00 | 0.456 | 12.51 | 2.00 | 0.401 |
| 12.42 | 2.50 | 0.558 | 12.03 | 2.50 | 0.588 | 12.25 | 2.50 | 0.570 | 12.47 | 2.50 | 0.501 |
| 12.38 | 3.00 | 0.669 | 12.07 | 3.00 | 0.705 | 12.25 | 3.00 | 0.684 | 12.43 | 3.00 | 0.601 |
| 12.31 | 3.50 | 0.781 | 12.15 | 3.50 | 0.823 | 12.25 | 3.50 | 0.799 | 12.40 | 3.50 | 0.702 |
| 12.20 | 4.00 | 0.892 | 12.14 | 4.00 | 0.940 | 12.17 | 4.00 | 0.913 | 12.34 | 4.00 | 0.802 |
| 11.54 | 4.50 | 1.004 | 11.42 | 4.50 | 1.058 | 11.57 | 4.50 | 1.027 | 12.17 | 4.50 | 0.902 |
| 11.19 | 5.00 | 1.115 | 11.16 | 5.00 | 1.175 | 11.38 | 5.00 | 1.141 | 11.49 | 5.00 | 1.002 |
| 11.05 | 5.50 | 1.227 | 11.04 | 5.50 | 1.293 | 11.24 | 5.50 | 1.255 | 11.21 | 5.50 | 1.103 |
| 10.97 | 6.00 | 1.338 | 10.96 | 6.00 | 1.410 | 11.15 | 6.00 | 1.369 | 11.11 | 6.00 | 1.203 |
| 10.87 | 6.50 | 1.450 | 10.91 | 6.50 | 1.528 | 11.03 | 6.50 | 1.483 | 11.02 | 6.50 | 1.303 |
| 10.81 | 7.00 | 1.561 | 10.84 | 7.00 | 1.645 | 10.96 | 7.00 | 1.597 | 10.97 | 7.00 | 1.403 |
| 10.76 | 7.50 | 1.673 | 10.79 | 7.50 | 1.763 | 10.91 | 7.50 | 1.711 | 10.92 | 7.50 | 1.504 |
| 10.72 | 8.00 | 1.784 | 10.74 | 8.00 | 1.880 | 10.86 | 8.00 | 1.825 | 10.87 | 8.00 | 1.604 |
| 10.68 | 8.50 | 1.896 | 10.70 | 8.50 | 1.998 | 10.81 | 8.50 | 1.939 | 10.82 | 8.50 | 1.704 |
| 10.63 | 9.00 | 2.007 | 10.68 | 9.00 | 2.115 | 10.76 | 9.00 | 2.053 | 10.77 | 9.00 | 1.804 |
| 10.59 | 9.50 | 2.119 | 10.66 | 9.50 | 2.233 | 10.73 | 9.50 | 2.168 | 10.73 | 9.50 | 1.905 |
| 10.55 | 10.00 | 2.230 | 10.61 | 10.00 | 2.350 | 10.69 | 10.00 | 2.828 | 10.70 | 10.00 | 2.005 |
| 10.52 | 10.50 | 2.342 | 10.57 | 10.50 | 2.468 | 10.64 | 10.50 | 2.396 | 10.66 | 10.50 | 2.105 |
| 10.48 | 11.00 | 2.453 | 10.53 | 11.00 | 2.585 | 10.60 | 11.00 | 2.510 | 10.63 | 11.00 | 2.205 |
| 10.44 | 11.50 | 2.565 | 10.49 | 11.50 | 2.703 | 10.57 | 11.50 | 2.624 | 10.59 | 11.50 | 2.306 |
| 10.41 | 12.00 | 2.676 | 10.45 | 12.00 | 2.820 | 10.53 | 12.00 | 2.738 | 10.57 | 12.00 | 2.406 |
| | | | 10.41 | 12.50 | 2.938 | 10.49 | 12.50 | 2.852 | 10.54 | 12.50 | 2.506 |
| | | | 10.38 | 13.00 | 3.055 | 10.46 | 13.00 | 2.966 | 10.51 | 13.00 | 2.606 |
| | | | | | | 10.42 | 13.50 | 3.080 | 10.49 | 13.50 | 2.707 |
| | | | | | | | | | 10.46 | 14.00 | 2.807 |
| | | | | | | | | | 10.44 | 14.50 | 2.907 |
| | | | | | | | | | 10.41 | 15.00 | 3.007 |

TABLE 4

10% Sodium Hydroxide

| Titration #12 12.40 g caustic | | | Titration #13 16.10 g cautic | | | Titration #14 17.49 g caustic | | |
|---|---|---|---|---|---|---|---|---|
| pH | mL phenol | equiv. phenol | pH | mL phenol | equiv. phenol | pH | mL phenol | equiv. phenol |
| 13.73 | 0.00 | 0.000 | 13.57 | 0.00 | 0.000 | 12.96 | 0.00 | 0.000 |
| 13.53 | 0.50 | 0.180 | 13.54 | 0.50 | 0.139 | 12.94 | 0.50 | 0.128 |
| 13.48 | 1.00 | 0.360 | 13.51 | 1.00 | 0.277 | 12.95 | 1.00 | 0.255 |
| 13.48 | 1.50 | 0.540 | 13.49 | 1.50 | 0.416 | 13.13 | 1.50 | 0.383 |
| 13.42 | 2.00 | 0.720 | 13.46 | 2.00 | 0.554 | 13.14 | 2.00 | 0.510 |
| 13.19 | 2.50 | 0.900 | 13.41 | 2.50 | 0.693 | 13.14 | 2.50 | 0.638 |
| 11.8 | 3.00 | 1.080 | 13.29 | 3.00 | 0.832 | 13.07 | 3.00 | 0.765 |
| 11.38 | 3.50 | 1.260 | 12.79 | 3.50 | 0.970 | 12.35 | 3.50 | 0.893 |
| 11.21 | 4.00 | 1.440 | 11.79 | 4.00 | 1.109 | 11.71 | 4.00 | 1.021 |
| 11.1 | 4.50 | 1.620 | 11.56 | 4.50 | 1.247 | 11.42 | 4.50 | 1.148 |
| 11.01 | 5.00 | 1.800 | 11.35 | 5.00 | 1.386 | 11.26 | 5.00 | 1.276 |
| 10.93 | 5.50 | 1.979 | 11.20 | 5.50 | 1.525 | 11.15 | 5.50 | 1.403 |
| 10.87 | 6.00 | 2.159 | 11.10 | 6.00 | 1.663 | 11.08 | 6.00 | 1.531 |
| 10.80 | 6.50 | 2.339 | 11.03 | 6.50 | 1.802 | 11.01 | 6.50 | 1.659 |
| 10.75 | 7.00 | 2.519 | 10.97 | 7.00 | 1.940 | 10.96 | 7.00 | 1.786 |
| 10.70 | 7.50 | 2.699 | 10.91 | 7.50 | 2.079 | 10.88 | 7.50 | 1.914 |
| 10.65 | 8.00 | 2.879 | 10.86 | 8.00 | 2.218 | 10.83 | 8.00 | 2.041 |
| 10.60 | 8.50 | 3.059 | 10.82 | 8.50 | 2.356 | 10.80 | 8.50 | 2.169 |
| 10.56 | 9.00 | 3.239 | 10.77 | 9.00 | 2.495 | 10.78 | 9.00 | 2.296 |
| 10.52 | 9.50 | 3.419 | 10.73 | 9.50 | 2.633 | 10.74 | 9.50 | 2.424 |
| 10.48 | 10.00 | 3.599 | 10.68 | 10.00 | 2.772 | 10.71 | 10.00 | 2.552 |
| 10.44 | 10.50 | 3.779 | 10.65 | 10.50 | 2.911 | 10.67 | 10.50 | 2.679 |
| 10.41 | 11.00 | 3.959 | 10.53 | 11.00 | 3.049 | 10.64 | 11.00 | 2.807 |
| 10.38 | 11.50 | 4.139 | 10.52 | 11.50 | 3.188 | 10.61 | 11.50 | 2.934 |
| 10.38 | 12.00 | 4.319 | 10.50 | 12.00 | 3.326 | 10.58 | 12.00 | 3.062 |
| 10.33 | 12.50 | 4.499 | 10.49 | 12.50 | 3.465 | 10.55 | 12.50 | 3.190 |
| 10.29 | 13.00 | 4.679 | | | | 10.52 | 13.00 | 3.317 |
| | | | | | | 10.50 | 13.50 | 3.445 |
| | | | | | | 10.47 | 14.00 | 3.572 |
| | | | | | | 10.45 | 14.50 | 3.700 |
| | | | | | | 10.42 | 15.00 | 3.827 |

TABLE 5

Composite Data for Examples 1–4

| Titration # | pH 1.0 eq. | pH 1.5 eq. | pH 2.0 eq. | pH 2.5 eq. | pH 3.0 eq. |
|---|---|---|---|---|---|
| 1 | 12.92 | 11.14 | 10.83 | 10.68 | |
| 2 | 11.71 | 10.97 | 10.79 | 10.58 | |
| 3 | 12.40 | 11.00 | 10.66 | 10.55 | |
| 4 | 11.88 | 11.24 | 11.00 | 10.75 | 10.59 |
| 5 | 11.70 | 10.91 | 10.65 | 10.48 | 10.32 |
| 6 | 12.37 | 10.95 | 10.61 | 10.38 | |
| 7 | 11.69 | 10.88 | 10.62 | 10.47 | |
| 8 | 11.54 | 10.87 | 10.63 | 10.48 | |
| 9 | 11.42 | 10.70 | 10.57 | 10.53 | 10.38 |
| 10 | 11.57 | 11.03 | 10.76 | 10.60 | 10.46 |
| 11 | 11.49 | 10.92 | 10.70 | 10.54 | 10.41 |
| 12 | 11.80 | 11.21 | 10.93 | 10.75 | 10.60 |
| 13 | 12.79 | 11.20 | 10.91 | 10.77 | 10.53 |
| 14 | 11.71 | 11.08 | 10.83 | 10.71 | 10.58 |
| Average | 11.92 | 11.00 | 10.75 | 10.59 | 10.48 |
| Std. Dev. | 0.49 | 0.15 | 0.13 | 0.12 | 0.11 |

What is claimed is:

1. A method for optimizing the use of an aqueous stream in a process for extracting phenol from a phenol containing organic stream, wherein:
the aqueous stream fed to the process comprises an alkali metal hydroxide;
said aqueous stream being fed to a phenol recovery system including a multistage scrubber unit having three tanks; the method comprising the steps of;
establishing an acceptable pH range for the aqueous stream;
measuring the pH of the aqueous stream as it exits the second of said three tanks, and
controlling a feed rate of the aqueous stream to the process, based on the pH of the aqueous stream.

2. A method for optimizing the use of an aqueous stream in a process for extracting phenol from a phenol containing organic stream, wherein:
the aqueous stream fed to the process comprises an alkali metal hydroxide, said aqueous stream being fed to a phenol recovery system, the method comprising the steps of;
establishing an acceptable pH range for the aqueous stream,
measuring the pH of the aqueous stream at a first point and a second point in the process, and
controlling a the feed rate of the aqueous stream to the process based on the pH at the first point and the second point.

3. The method of claim 2, further comprising the steps of establishing a first acceptable pH range for the first point, and establishing a second acceptable pH range for the second point.

4. The method of claim 3, wherein the first acceptable pH range and the second acceptable pH range are not the same.

5. The method according to claim 4, wherein the first acceptable pH range corresponds to approximately 1 equivalent of phenol having been extracted into the aqueous stream, relative to alkali metal hydroxide in the aqueous stream fed to the process, and
the second acceptable pH range corresponds to greater than 1 equivalent of phenol having been extracted into the aqueous stream, relative to alkali metal hydroxide in the aqueous stream fed to the process.

6. The method of claim 5, wherein the aqueous stream fed to the process comprises sodium hydroxide.

7. The method of claim 6, wherein the concentration of sodium hydroxide in the aqueous stream is about 10% to about 30%.

8. The method of claim 7, wherein the concentration of sodium hydroxide in the aqueous stream is about 20%.

9. The method of claim 8, wherein the first acceptable pH range is from about 11 to about 12, and the second acceptable pH range is about 9.7 to about 10.7.

10. The method of claim 9, wherein the phenol recovery system is a multi-stage scrubber unit comprising a plurality of tanks wherein the aqueous stream and phenol containing organic stream are contacted in counter-current flow.

11. The method of claim 10, wherein the multi-stage scrubber unit has three tanks, and the pH of the aqueous stream is measured at the first point as it exits the second tank, and the pH is measured at the second point as it exits the third tank.

12. The method of claim 11, wherein; the phenol content in the phenol containing organic stream is reduced to less than 100 ppm.

13. The method of claim 12, wherein the phenol content in the phenol containing organic stream is reduced to less than 25 ppm.

14. A method for determining the quantity of phenol that has been extracted into an aqueous stream containing an alkali metal hydroxide, the method comprising the steps of;
developing a curve relating the pH of an aqueous solution containing an alkali metal hydroxide to the equivalents of phenol extracted into the solution, determining the initial concentration of alkali metal hydroxide in an aqueous stream, exposing the aqueous stream to a phenol containing organic stream, such that phenol is extracted into the aqueous stream, determining the pH of the aqueous stream having extracted phenol from the phenol containing organic stream, relating the pH of the aqueous stream to a point on the curve, corresponding to a number of equivalents of phenol extracted into the aqueous stream, and calculating the concentration of phenol in the aqueous stream from the number of equivalents of phenol and the initial concentration of alkali metal hydroxide.

15. The method of claim 14, wherein the alkali metal hydroxide is sodium hydroxide.

* * * * *